US010377683B2

(12) United States Patent
Nenu et al.

(10) Patent No.: US 10,377,683 B2
(45) Date of Patent: Aug. 13, 2019

(54) ISOMERISATION CATALYST PREPARATION PROCESS

(75) Inventors: Cristina Nicoleta Nenu, Villanova, PA (US); Bart Pelgrim, Amsterdam (NL); Ingrid Maria van Vegchel, Amsterdam (NL)

(73) Assignee: SHELL OIL COMPANY, Houston, TX (US)

(*) Notice: Subject to any disclaimer, the term of this patent is extended or adjusted under 35 U.S.C. 154(b) by 118 days.

(21) Appl. No.: 13/885,964

(22) PCT Filed: Nov. 16, 2011

(86) PCT No.: PCT/EP2011/070195
§ 371 (c)(1),
(2), (4) Date: Oct. 21, 2013

(87) PCT Pub. No.: WO2012/066013
PCT Pub. Date: May 24, 2012

(65) Prior Publication Data
US 2014/0039234 A1 Feb. 6, 2014

(30) Foreign Application Priority Data
Nov. 18, 2010 (EP) .................... 10191707

(51) Int. Cl.
C07C 5/27 (2006.01)
B01J 23/42 (2006.01)
B01J 29/70 (2006.01)
B01J 29/74 (2006.01)
B01J 37/00 (2006.01)
B01J 37/02 (2006.01)
C07C 15/08 (2006.01)

(52) U.S. Cl.
CPC ............ C07C 5/2737 (2013.01); B01J 23/42 (2013.01); B01J 29/7034 (2013.01); B01J 29/7469 (2013.01); B01J 37/0009 (2013.01); B01J 37/0201 (2013.01); B01J 37/0213 (2013.01); C07C 5/2708 (2013.01); C07C 5/2775 (2013.01); B01J 2229/42 (2013.01); C07C 2529/44 (2013.01); C07C 2529/74 (2013.01); Y02P 20/52 (2015.11)

(58) Field of Classification Search
CPC combination set(s) only.
See application file for complete search history.

(56) References Cited

U.S. PATENT DOCUMENTS

| 3,832,449 | A | | 8/1974 | Rosinski et al. |
| 3,856,872 | A | | 12/1974 | Morrison |
| 4,485,185 | A | | 11/1984 | Onodera et al. |
| 4,762,957 | A | | 8/1988 | Sachtler et al. |
| 4,874,504 | A | * | 10/1989 | von Ballmoos ......... B01J 29/62 208/111.01 |
| 4,899,012 | A | | 2/1990 | Sachtler et al. |
| 4,939,110 | A | | 3/1990 | Sachtler et al. |
| 5,053,558 | A | * | 10/1991 | Sachtler ................ C07C 5/2791 568/780 |
| 6,207,871 | B1 | * | 3/2001 | Hellring ................ C07C 5/2767 585/474 |
| 6,576,120 | B1 | | 6/2003 | van Ballegoy et al. |
| 6,652,832 | B2 | | 11/2003 | Malek |
| 7,368,620 | B2 | | 5/2008 | Zhou et al. |
| 9,199,894 | B2 | | 12/2015 | Nenu et al. |
| 2006/0030478 | A1 | * | 2/2006 | Raich .................... B01J 29/068 502/66 |
| 2007/0004947 | A1 | | 1/2007 | Zhou et al. ................. 585/481 |
| 2008/0035525 | A1 | * | 2/2008 | Burgfels ............. B01J 29/7034 208/26 |

FOREIGN PATENT DOCUMENTS

| CN | 1376089 | 10/2002 | |
| CN | 1715370 | 1/2006 | |
| CN | 1330699 | 8/2007 | |
| CN | 101208283 | 6/2008 | |
| EP | 1547684 | 6/2005 | ............. B01J 29/70 |
| WO | 199745198 | 12/1997 | |
| WO | 2004046034 | 6/2004 | |
| WO | WO2010000652 | 1/2010 | ............. B01J 29/74 |
| WO | WO 2010000652 A1 * | 1/2010 | |

OTHER PUBLICATIONS

Miller, et al. "A fundamental study of platinum tetraammine impregnation of silica 2. The effect of method of preparation, loading, and calcination temperature on (reduced) particle size". Journal of Catalysis 225 (2004) 203-212.*
Spieker et al. "A fundamental model of platinum impregnation onto alumina", Chemical Engineering Science 56 (2001) 3491-3504.*
PCT International Search Report, Application No. PCT/EP2011/070193 dated Feb. 6, 2012.
Smirniotis P.G. et al., "Effect of the Si/Al Ration and of the Zeolite Structure on the Performance of Dealuminated Zeolites for the Reforming of Hydrocarbon Mixtures", Ind. Eng. Chem. Res., vol. 35, No. 9, 1996, pp. 3055-3066.
Zhang W. et al., "Dealuminated Zeolite-Based Composite Catalysts for Reforming of an Industrial Naphthene-Rich Feedstock", Applied Catalysis A: General, Elsevier Science, Amsterdam, NL, vol. 168, No. 1, 1998, pp. 113-130.

(Continued)

Primary Examiner — In Suk C Bullock
Assistant Examiner — Ali Z Fadhel
(74) Attorney, Agent, or Firm — Charles W. Stewart

(57) ABSTRACT

A process for preparing an alkylaromatics isomerisation catalyst comprising at least 0.01% wt of platinum on a carrier comprising of from 1 to 9 wt % of ZSM-12 and inorganic binder, which process comprises treating the carrier with an impregnation solution comprising base and an anionic platinum complex which impregnation solution has a pH of from 5.5 to 8; and a process for the isomerisation of alkylaromatics with the help of catalyst thus obtained.

22 Claims, No Drawings

(56) References Cited

OTHER PUBLICATIONS

PCT International Search Report completed Feb. 6, 2012, for Application No. PCT/EP2011/070195 filed Nov. 1, 2011.
State Intellectual Property Office of the Peoples Republic of China, 1st office action dated Jun. 19, 2014 for, Chinese Application No. 201180062617.0.

* cited by examiner

ISOMERISATION CATALYST PREPARATION PROCESS

PRIORITY CLAIM

The present application claims priority from PCT/EP2011/070193, filed Nov. 16, 2011, which claims priority from European application 10191702.9, filed Nov. 18, 2010, which is incorporated herein by reference.

This invention relates to a zeolite-based catalyst for the isomerisation of alkylaromatics, more specifically ethylbenzene.

Following fractionation or distillation of crude petroleum oil, a straight-run naphtha fraction is obtained. This fraction generally boils the 70° C. to 190° C. range, more specifically 80° C. to 150° C. at atmospheric pressure.

This naphtha fraction may be catalytically converted to an aromatic reformate. On conversion to reformate, the aromatics content is considerably increased and the resulting hydrocarbon mixture becomes highly desirable as a source of valuable chemical intermediates and as a component for gasoline.

The aromatic hydrocarbons present in the reformate generally contain 8 carbon atoms and include but are not limited to ethylbenzene and xylenes. Other components may be present such as their hydrogenated homologues for example naphthenes.

In many instances, it is desirable to further increase the content of highly desirable compounds by further conversion of aromatics. Many catalysts have been made and proposed for these reactions.

Within the xylenes, para-xylene is often the most desirable compound. O-xylene is the most desirable compound in only slightly less instances. Meta-xylene tends to be the least desirable compound. Isomerisation or transalkylation processes have been developed to specifically increase the amount of para-xylene or sometimes o-xylene. However, these processes tend to produce undesired side-products as mentioned above.

WO-A-2010/000652 describes alkylaromatics isomerisation catalysts comprising platinum on a carrier comprising 1-9 wt % ZSM-12 zeolite. Although these catalyst show a good performance, there is a continuous desire for further improvement. An important aspect of the performance of a catalyst is its activity. If a process is required to operate at high feed throughput, a high activity is crucial.

US-A-2007/0004947 describes an alkylaromatics isomerisation process using a first catalyst which is substantially free of a platinum-group metal and a second catalyst which comprises platinum-group metal and 10 to 90 mass-% of at least one molecular sieve. The platinum preferably is concentrated on the binder component which can be achieved by compositing the metal component with the binder prior to co-extruding the sieve and binder. To obtain 0.3 mass-% platinum by impregnation, the solution of Comparative Example 1 of US-A-2007/0004947 must have had a relatively high concentration of chloroplatinic acid causing its pH to be less than 5.5. Furthermore, the catalyst is sulfided to yield a catalyst containing 0.1% wt of sulphur.

The present invention relates to alkylaromatics isomerisation catalysts having improved activity. This improvement is attained by the use of a specific neutral impregnation solution. WO-A-2010/000652 does not mention the pH of the platinum containing impregnation solution used. The impregnation exemplified in WO-A-2010/000652 was carried out at a pH below 3.

It has now surprisingly been found that the specific impregnation solution of the present invention gives isomerisation catalysts having improved activity.

A further advantage of the catalyst prepared according to the present invention is that it has been found that this catalyst increases the proportion of ortho-xylene in the isomerisation product.

An object of the present invention is to prepare more active catalyst for the isomerisation of alkylaromatics more specifically for the isomerisation of a feed of alkylaromatics comprising 8 carbon atoms to obtain a product having an increased xylenes content and/or an increased ortho-xylene content. For this, ethylbenzene is to be converted into xylene and/or meta-xylene into ortho-xylene.

The present invention provides a process for preparing an alkylaromatics isomerisation catalyst comprising at least 0.01% wt of platinum on a carrier comprising of from 1 to 9 wt % of ZSM-12 and inorganic binder, which process comprises treating the carrier with an impregnation solution comprising base and an anionic platinum complex which impregnation solution has a pH of from 5.5 to 8.

Weight amounts mentioned in this application are on total weight of catalyst unless mentioned otherwise.

The expression isomerisation is used to indicate rearrangement of the carbons atoms within a molecule without substantially changing the number of carbon atoms of a molecule.

It is unexpected that a neutral impregnation solution according to the present invention gives an improved activity.

The catalyst prepared according to the present invention can be used with a wide range of alkylaromatic compounds such as alkylaromatics comprising 8 carbon atoms or more, more specifically of from 8 to 12 carbon atoms. Preferably, the hydrocarbon feed mainly consists of alkylaromatic compounds comprising of from 8 to 10, more specifically of from 8 to 9, carbon atoms. The isomerisation of these compounds is known to follow similar reaction paths and uses the same or similar catalyst formulations. More specifically, the feed consists of at least 50% wt, more specifically at least 60% wt, most specifically at least 70% wt of alkylaromatic compounds comprising of from 8 to 10, more specifically of from 8 to 9, carbon atoms. Therefore, the present invention relates to the preparation of a catalyst for isomerisation of alkylaromatics in general, more specifically alkylaromatics comprising of from 8 to 10 carbons, more specifically alkylaromatics comprising 8 or 9 carbon atoms.

The impregnation solution for use in the present catalyst preparation process comprises an anionic platinum complex. The expression anionic platinum complex is used to indicate that the complex containing platinum and the ligands, more specifically the chloride ligands, has a negative charge.

Platinum complexes which are especially preferred are platinum chloride complexes more specifically complexes according to the general formula $X_nPtCl_m$ in which X is a cation, n is an integer of from 1 to 6, preferably of from 2 to 4, most preferably 2, and m is an integer of from 4 to 8, most preferably 6. X preferably is selected from the group consisting of ammonium and hydrogen. Most preferably, hexachloroplatinic acid is used. The hexachloroplatinic acid can be either added as such or can be prepared in-situ.

It will be appreciated that the impregnation solution generally will contain the complex in the dissolved form and not as the complex as such. The complexes generally are added to water to obtain the desired impregnation solution. However, it also is possible to form the complex in the impregnation solution by adding the required constituents as part of other complexes or compounds.

The pH of the impregnation solution is of from 5.5 to 8. Preferably the pH is at least 6, more preferably more than 6. The pH preferably is less than 8, more preferably at most 7.5.

The desired pH is obtained by adding a base. The base can be any base known to be suitable to someone skilled in the art. Residue of the base which remains on or in the catalyst after calcination should not negatively interfere with the catalytic properties of the final catalyst. For this reason, it is generally preferred to use a basic compound according to the formula $(R_1R_2R_3NH)OH$ in which the compounds $R_1$, $R_2$, $R_3$ each independently are chosen from the group consisting of hydrogen and alkyl, more specifically chosen from the group consisting of hydrogen and an alkyl containing of from 1 to 6 carbon atoms, most specifically of from 1 to 4 carbon atoms. This class of compounds tends to be removed in full during calcination. Most preferably, the base is ammonium hydroxide.

Impregnation can be carried out in any way known to someone skilled in the art such as pore volume impregnation and so-called continuously stirred impregnation. The latter method is preferred for the present invention and involves contacting the carrier with an excess of impregnation solution while stirring. The impregnated carrier is subsequently removed from the impregnation solution.

The impregnated carrier is preferably dried and calcined after impregnation. Drying and calcining is generally carried out at a temperature of from 300 to 600° C.

It is preferred not to sulphide the catalyst before use. The dried and calcined catalyst preferably contains less than 0.1% wt of sulphur, based on total amount of catalyst, more specifically less than 0.09% wt, more specifically less than 0.08% wt, more specifically less than 0.07% wt, most specifically less than 0.05% wt.

The inorganic binder preferably is acidic and may be selected from any of the suitable refractory metal oxides known in the art. The binder can be non-acidic when added but be converted into an acidic binder during calcination. For example, pseudo-boehmite converts into acidic gamma-alumina during calcination. Examples of preferred acidic inorganic binders is alumina optionally in combination with other compounds such as silica, alumina, titania, zirconia, ceria and/or gallia. Preferably, the binder consists of alumina with up to 50% wt of other compounds, more specifically up to 20% wt, more specifically up to 10% wt, most specifically up to 5% wt. Preferably, the binder consists of acidic alumina.

Alumina can be prepared in a number of forms. The alumina grades available differ in parameters such as pore volume, average pore diameter, bulk density, and surface area. Although different alumina manufacturers can provide the same or similar alumina products under different nomenclature, different products classifications can have the same or similar or overlapping criteria and/or properties. For example, "high pore" and "wide pore" aluminas tend to have the same or similar properties.

The present invention extends to the use of alumina as the inorganic binder from any source, and examples of suitable alumina binders include grades of the Pural range from Sasol, such as the KR and SB grades, and other wide pore aluminas such as WPA and HMPA from Criterion.

In a preferred embodiment of the present invention, the pore volume of the inorganic binder as measured with the help of nitrogen is at least 0.6 cc/g, preferably at least 1.2 cc/g; and the pore volume of the inorganic binder is up to 2 cc/g, preferably up to 1.6 cc/g.

These ranges of pore volume of the inorganic binder include 'wide pore' alumina, which has a more open structure to allow greater interaction with the alkylaromatics.

In another embodiment of the present invention, the average pore diameter of the inorganic binder is greater than 80 Å, preferably greater than 90 Å.

In a further embodiment of the present invention, the bulk density of the inorganic binder is less than 0.3, preferably less than 0.25 g/cc.

In a yet further embodiment of the present invention, the inorganic binder is present in an amount of more than 50% wt, more specifically more than 70 wt %, preferably more than 80 wt %, especially at least 90 wt %, based on total amount of catalyst.

The catalyst includes at least 0.01 wt % of platinum. Besides platinum, one or more other metals such as nickel and palladium can be present. Preferably, only platinum is present. The amount of platinum preferably is at least 0.05% wt, more preferably in the range of from 0.1 to 0.6 wt % based on total weight of catalyst.

The zeolite ZSM-12 is a well known zeolite, generally having an aluminosilicate basis, optionally including one or more other elements. Many methods of making various forms of ZSM-12 are known in the art. A definition of ZSM-12 is given in the Database of Zeolite Structures published in 2007/2008 on behalf of the Structure Commission of the International Zeolite Association.

The catalyst could be provided by admixture of the inorganic binder and zeolite components, following by shaping, and then typically drying and calcining the pre-former product. Optionally, the addition of the platinum complex is carried out after drying and/or calcining of the catalyst carrier. Preferably, the catalyst carrier is prepared by extrusion. Therefore, the catalyst carrier preferably is an extrudate.

In the present invention, it is particularly preferred that the ZSM-12 zeolite has:
 an average crystal size in the range of 30 to 70 nm; and/or
 a surface area as measured with the help of nitrogen adsorption of more than 250 $m^2$/g, preferably more than 280 $m^2$/g.

The size of the zeolite crystallites is determined by using X-ray diffraction and the Scherrer equation.

Additionally, it is preferred that the crystallinity of ZSM-12 is greater than 94%, preferably greater than 97%.

The zeolite as described above is known to those skilled in the art and is not further described herein.

The proportion of the catalyst being the ZSM-12 zeolite is preferably in the range 1-7 wt %, preferably 1-5 wt %, especially 3-5 wt %, based on total amount of catalyst. Whilst the catalyst of the present invention may include a minor or very small amount of zeolite other than ZSM-12, the catalyst preferably comprises only ZSM-12 as the zeolite.

Another parameter of the zeolite ZSM-12 is its silica to alumina molar ratio (SAR). In the ethylbenzene isomerisation process, two different reactions overlap: ethylbenzene isomerisation and xylene isomerisation. Both reactions need acid sites to occur, and the acidity of the zeolite conventionally has been considered as having to be moderate. For this reason, conventional commercial catalysts have low SAR, and conventionally, it has been desired to maintain a relatively low SAR.

It is a particular feature of the present invention that the SAR of the zeolite preferably is in the range of from 60 to 200, more preferably in the range 70 to 150. This is because of the recognition that the acidity of inorganic binder can also contribute to the acidity of the catalyst for the reaction. Similarly, it was expected that a higher loading of zeolite in the catalyst would increase the catalyst activity. However, this turned out not to be required. The catalyst of the present invention has a lower than expected zeolite proportion namely at most 9 wt %, more specifically at most 8% wt, more specifically at most 7% wt and in particular less than 6.5 wt % based on total amount of catalyst.

The alkylaromatics isomerisation catalyst preferably consists of acidic inorganic binder, ZSM-12 zeolite having a SAR of from 60 to 200 and at least 0.1% wt of platinum.

The catalyst of the present invention is particularly suitable for the hydroisomerisation of ethylbenzene to xylenes, and for the isomerisation of xylenes to equilibrium. Further particularly, the catalyst of the present invention is suitable for use to provide para-xylene from ethylbenzene and other isomers of xylene commonly provided in mixed-component streams.

According to a further aspect of the present invention, there is provided a process for the isomerisation of alkylaromatics to provide a reaction mixture, which process comprises contacting a hydrocarbon stream comprising alkylaromatics with a catalyst prepared according to the present invention.

The hydrocarbon stream may comprise any amount of ethylbenzene, such as more than 60 wt % based on total amount of feedstock. The hydrocarbon stream specifically contains at most 60 wt % of ethylbenzene, more specifically at most 50% wt. Preferably, the hydrocarbon stream comprises at least 1% wt of ethylbenzene, more preferably at least 2% wt, more preferably at least 3% wt, more specifically at least 5% wt, more specifically at least 8% wt, preferably at least 10% wt, most preferably at least 15 wt %.

The hydrocarbon feed preferably is contacted with the catalyst at a temperature in the range of from 300 to 450° C., preferably at least 350° C. and preferably at most 400° C. Preferably, the pressure during isomerisation is of from 2 to 20 bar, more specifically of from 3 to 15 bar. The molar ratio of hydrogen to hydrocarbon of the feed preferably is of from 1 to 15 mol/mol, more specifically of from 2 to 10 mol/mol.

Of the xylenes present in the hydrocarbon feed, at least 20% generally will be in the form of meta-xylene, more specifically at least 30%, more specifically at least 40%, preferably at least 50%, more preferably at least 60%, most preferably at least 70%.

Examples of the present invention will now be described by way of example only.

EXAMPLES

Example 1 (Comparative)

A ZSM-12/alumina catalyst support was prepared from 5wt % of ZSM-12 having a SAR of 95, and 95 wt % of Criterion WPA alumina.

The mixture was kneaded and then shaped by extrusion into 1.6 mm cylinders. The extrudates were dried at 120° C. and subsequently calcined in air at 550° C. for 4 hours.

These extrudates were impregnated by pore volume impregnation using an impregnation solution comprising hexachloroplatinic acid ($H_2PtCl_6$) as the metal source with nitric acid added to obtain pH of 1.6.

The extrudates thus obtained were dried at 120° C. and subsequently statically calcined at 475° C. for 1 hour.

The final catalyst contained 0.3% wt of platinum based on total weight of catalyst.

Example 2

An impregnation solution was prepared comprising $(NH_4)_2PtCl_6$ as the metal source with $NH_4OH$ added to the impregnation solution to obtain a pH of 7.

Freshly dried extrudates prepared as described in Example 1 were contacted with an excess of this impregnation solution and the mixture was continuously stirred.

The impregnated extrudates were separated from the impregnation solution and excess solution was removed. The extrudates thus obtained were dried at 120° C. and subsequently calcined statically at a temperature of 475° C. for 1 hour.

The final catalyst contained 0.3% wt of platinum based on total weight of catalyst.

Example 3

An impregnation solution was prepared comprising hexachloroplatinic acid ($H_2PtCl_6$) as the metal source with triethanolamine added to obtain a pH of 7.

Freshly dried extrudates prepared as described in Example 1 were contacted with an excess of this impregnation solution and the mixture was continuously stirred.

The impregnated extrudates were separated from the impregnation solution and excess solution was removed. The extrudates thus obtained were dried at 120° C. and subsequently calcined statically at a temperature of 475° C. for 1 hour.

The final catalyst contained 0.3% wt of platinum based on total weight of catalyst.

Example 4 (Comparative)

Extrudates as described in Example 1 were impregnated by pore volume impregnation using an impregnation solution comprising $Pt(NH_3)_4(NO_3)_2$ as the metal source with ammoniumhydroxide added to obtain pH of 8.5.

The pore volume impregnated extrudates were dried at 120° C. and subsequently statically calcined at 475° C. for 1 hour.

The final catalyst contained 0.3% wt of platinum based on total weight of catalyst.

Example 5

The catalysts prepared in the above Examples were tested in the isomerisation of an ethylbenzene and mixed xylene mixture (comprising 19 wt % ethylbenzene (EB), 15.5 wt % ortho-xylene (OX), 59 wt % meta-xylene (MX) and 6.5 wt % ethyl cyclohexane).

The catalytic test was performed in a micro-flow reactor unit encompassing a reactor tube with an internal diameter of 15 mm, into which the catalyst was loaded together with SiC as packing material. After loading the catalyst was dried at 400° C. for 1.5 hours and then reduced with $H_2$ at 400° C. for 1 hour at a pressure of 8 bar. The reactor was then heated to 425° C. and treated with a mixture of 20 wt % EB and 80 wt % meta-xylene for a period of 24 hours at a weight hourly space velocity (WHSV) of 5 g feed/g catalyst/h and a $H_2$/hydrocarbon ratio of 4 mol/mol to reach a stable operation regime. Following this, the catalyst was subjected to a temperature of 387° C. and treated with the same EB and mixed xylene mixture described above (19 wt % EB, 15.5 wt % OX, 59 wt % MX and 6.5 wt % ethyl cyclohexane) at a WHSV of 4.5 g feed/g catalyst/h and a $H_2$/hydrocarbon ratio of 4 mol/mol.

The following expressions hereinafter have the following meaning.

Ethylbenzene conversion (EB conversion) is the weight percent of ethylbenzene converted by the catalyst into a xylene, i.e. either ortho-, meta- or para-xylene.

PXate is a measure for the degree to which the xylene reaction mixture has reached equilibrium for para-xylene. It is defined as follows:

$$PXate = \frac{\%\ w\ PX\ \text{in Xylenes in product} - \%\ w\ PX\ \text{in Xylenes in feed}}{\%\ w\ PX\ \text{in Xylenes in equilibrium} - \%\ w\ PX\ \text{in Xylenes in feed}} \times 100\%$$

where PX stands for para-xylene.

The EB conversion was extrapolated to a PXate of 95% wt on basis of the experimental data. A PXate of 95% wt is often applied as a reference point for commercial purposes.

The results can be seen in Table 1.

TABLE 1

|  | pH of impregnation solution | EB conversion (% wt) at PXate of 95 (% wt) |
|---|---|---|
| Comparative Example 1 | 1.6 | 33.8 |
| Example 2 | 7 | 37.0 |
| Example 3 | 7 | 37.0 |
| Comparative Example 4 | 8.5 | 35.7 |

It will be clear from Table 1 that the neutral impregnated catalysts of Examples 2 and 3 of the present invention have an improved activity in that a higher amount of ethylbenzene is converted at a PXate of 95% wt than with the acid impregnated catalyst of Comparative Example 1 or the basic impregnated catalyst of Comparative Example 4.

That which is claimed is:

1. A process for preparing an alkylaromatics isomerization catalyst, comprising:
    mixing an amount of ZSM-12 zeolite with an amount of an alumina binder to form a mixture, wherein said ZSM-12 zeolite has an average crystal size in the range of from 30 to 70 nm, a surface area of more than 250 m²/g as measured by nitrogen adsorption, and crystallinity of greater than 94%, and wherein the alumina of said alumina binder has a nitrogen pore volume of at least 0.6 cc/g and an average pore diameter greater than 80 Å;
    shaping said mixture into extrudates;
    without prior calcination of said extrudates, impregnating said extrudates with an impregnation solution comprising a base and an anionic platinum complex to provide impregnated extrudates, wherein said impregnation solution has a pH of from 5.5 to 8;
    drying said impregnated extrudates; and
    calcining the dried impregnated extrudates at a calcination temperature in the range of from 300 to 600° C. to provide said alkylaromatics isomerization catalyst;
    wherein said amount of ZSM-12 zeolite and said amount of said alumina binder are such as to provide said alkylaromatics isomerization catalyst that comprises from 1 to 9 wt % ZSM-12 zeolite and more than 50 wt % alumina binder, based on the total weight of said alkylaromatics isomerization catalyst;
    wherein the alkylaromatics isomerization catalyst provides an ethylbenzene conversion of at least 37% wt at a PXate of 95 wt %.

2. A process as claimed in claim 1 in which the base is a compound according to the formula $(R_1R_2R_3NH)OH$ in which the compounds $R_1$, $R_2$, $R_3$ each independently are chosen from the group consisting of hydrogen and alkyl containing of from 1 to 6 carbon atoms.

3. A process as claimed in claim 1 in which the impregnation is carried out by contacting the extrudates with an excess of impregnation solution while stirring.

4. A process as claimed in claim 1 in which a silica to alumina molar ratio of the ZSM-12 is in the range of from 60 to 200.

5. A process as claimed in claim 1 in which the anionic platinum complex is a platinum chloride complex of the general formula $X_nPtCl_m$, wherein X is either ammonium or hydrogen, n is an integer of from 1 to 6, and m is an integer of from 4 to 8.

6. A process as claimed in claim 1, wherein the alumina binder is present in the alkylation isomerization catalyst in an amount of at least 90 wt %.

7. A process as claimed in claim 6, wherein the alumina binder further comprises an additional compound selected from the group consisting of silica, titania, zirconia, ceria and gallia.

8. A process as claimed in claim 7, wherein the alumina binder contains up to 50% wt of the additional compound.

9. A process as claimed in claim 8, wherein a silica-to-alumina molar ratio of the ZSM-12 zeolite is in the range of from 70 to 150.

10. A process as claimed in claim 5, wherein the platinum chloride complex is hexachloroplatinic acid.

11. A process as claimed in claim 10, wherein the alumina binder is present in the extrudates in an amount of more than 80 wt %.

12. A process as claimed in claim 11, wherein the alkylaromatics isomerization catalyst comprises from 1 to 7 wt % of the ZSM-12 zeolite.

13. A process as claimed in claim 12, wherein the alumina binder further comprises an additional compound selected from the group consisting of silica, titania, zirconia, ceria and gallia.

14. A process as claimed in claim 13, wherein the alumina binder contains up to 10% wt of the additional compound.

15. A process for preparing an alkylaromatics isomerization catalyst comprising:
    mixing an amount of ZSM-12 zeolite with an amount of an alumina binder to form a mixture, wherein said ZSM-12 zeolite has an average crystal size in the range of from 30 to 70 nm, a surface area of more than 250 m²/g as measured by nitrogen adsorption, and crystallinity of greater than 94%, and wherein the alumina of said alumina binder has a nitrogen pore volume of at least 0.6 cc/g and an average pore diameter greater than 80 Å;
    shaping said mixture into preformed carrier particles;
    drying said preformed carrier particles;
    calcining the dried preformed carrier particles at a calcination temperature in the range of from 300 to 600° C. to provide dried and calcined preformed carrier particles;
    impregnating said dried and calcined preformed carrier particles with an impregnation solution comprising a base and an anionic platinum complex to provide impregnated preformed carrier particles, wherein said impregnation solution has a pH of from 5.5 to 8;

drying said impregnated preformed carrier particles; and calcining the dried impregnated preformed carrier particles at a calcination temperature in the range of from 300 to 600° C. to provide said alkylaromatics isomerization catalyst;

wherein said amount of ZSM-12 zeolite and said amount of said alumina binder are such as to provide said alkylaromatics isomerization catalyst that comprises from 1 to 9 wt % ZSM-12 zeolite and more than 50wt % alumina binder, based on the total weight of said alkylaromatics isomerization catalyst;

wherein the alkylaromatics isomerization catalyst provides an ethylbenzene conversion of at least 37% wt at a PXate of 95 wt %.

16. A process as claimed in claim 15 in which the base is a compound according to the formula $(R_1R_2R_3NH)OH$ in which the compounds $R_1$, $R_2$, $R_3$ each independently are chosen from the group consisting of hydrogen and alkyl containing of from 1 to 6 carbon atoms.

17. A process as claimed in claim 16 in which a silica to alumina molar ratio of the ZSM-12 zeolite is in the range of from 60 to 200.

18. A process as claimed in claim 17, wherein the anionic platinum complex is platinum chloride complex, and wherein the platinum chloride complex is hexachloroplatinic acid.

19. A process as claimed in claim 18, wherein the alumina binder is present in carrier in an amount of more than 80 wt %.

20. A process as claimed in claim 19, wherein the alkylaromatics isomerization catalyst comprises from 1 to 7 wt % of the ZSM-12 zeolite.

21. A process as claimed in claim 20, wherein the alumina binder further comprises an additional compound selected from the group consisting of silica, titania, zirconia, ceria and gallia.

22. A process as claimed in claim 21, wherein the alumina binder contains up to 10% wt of the additional compound.

* * * * *